(12) United States Patent
Chen

(10) Patent No.: US 6,706,074 B1
(45) Date of Patent: Mar. 16, 2004

(54) ARTIFICIAL KNEE JOINT ASSEMBLY CAPABLE OF MAINTAINING A KNEE ANGLE BETWEEN A LOWER LEG AND A THIGH WHEN THE ASSEMBLY STANDS ON A HORIZONTAL OR INCLINED SURFACE

(76) Inventor: Sen-Jung Chen, No. 236, Sec. 3, Ho-Ping W. Rd., Taipei City (TW)

( * ) Notice: Subject to any disclaimer, the term of this patent is extended or adjusted under 35 U.S.C. 154(b) by 0 days.

(21) Appl. No.: 10/421,551
(22) Filed: Apr. 22, 2003
(51) Int. Cl.[7] ................................................ A61F 2/64
(52) U.S. Cl. ......................................................... 623/44
(58) Field of Search ............................. 623/39, 40, 41, 623/42, 43, 44, 45, 46

(56) References Cited

U.S. PATENT DOCUMENTS

| | | | | |
|---|---|---|---|---|
| 2,672,618 A | * | 3/1954 | Haag ................................. 3/27 |
| 4,179,759 A | * | 12/1979 | Smith ................................ 3/24 |
| 5,376,137 A | * | 12/1994 | Shorter et al. ................. 623/44 |
| 5,779,735 A | * | 7/1998 | Molino ........................... 623/44 |
| 6,106,560 A | * | 8/2000 | Boender ........................ 623/44 |
| 6,117,177 A | * | 9/2000 | Chen et al. .................... 623/44 |
| 6,206,933 B1 | * | 3/2001 | Shorter et al. ................. 623/44 |

FOREIGN PATENT DOCUMENTS

WO 92/22267 * 12/1992

* cited by examiner

Primary Examiner—Bruce E Snow
(74) Attorney, Agent, or Firm—Ladas & Parry (57) ABSTRACT

An artificial knee joint assembly includes a knee seat connected fixedly to a residual thigh, a support frame connected to the knee seat by means of a linkage unit, a prosthetic lower leg connected pivotally to a lower end of the support frame, a hydraulic cylinder unit disposed within the support frame so as to dampen the movement of the support frame relative to the knee seat, and a valve assembly disposed within the support frame. When the lower leg stands on a horizontal or inclined surface, the valve assembly is actuated by the lower leg to stop the operation of the hydraulic cylinder unit, thereby preventing rotation of the lower leg relative to the thigh.

7 Claims, 6 Drawing Sheets

FIG. 10

ARTIFICIAL KNEE JOINT ASSEMBLY CAPABLE OF MAINTAINING A KNEE ANGLE BETWEEN A LOWER LEG AND A THIGH WHEN THE ASSEMBLY STANDS ON A HORIZONTAL OR INCLINED SURFACE

BACKGROUND OF THE INVENTION

1. Field of the Invention

This invention relates to an artificial knee joint assembly, and more particularly to a safety artificial knee joint assembly, which can maintain a knee angle between a lower leg and a thigh when the assembly stands on a horizontal or inclined surface.

2. Description of the Related Art

Figure 1:
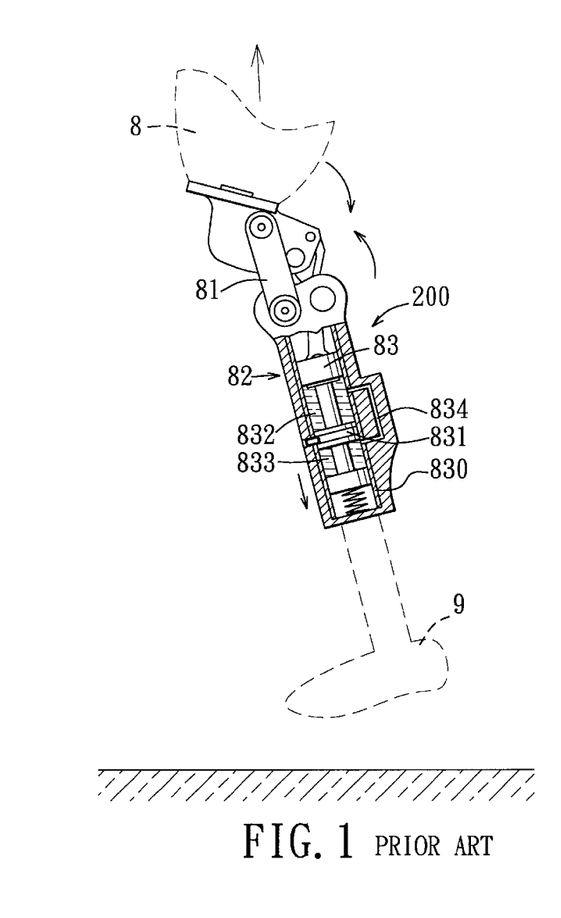
FIG. 1 illustrates how a prosthetic lower leg of a conventional knee joint assembly is pulled away from the ground.
Figure 2:
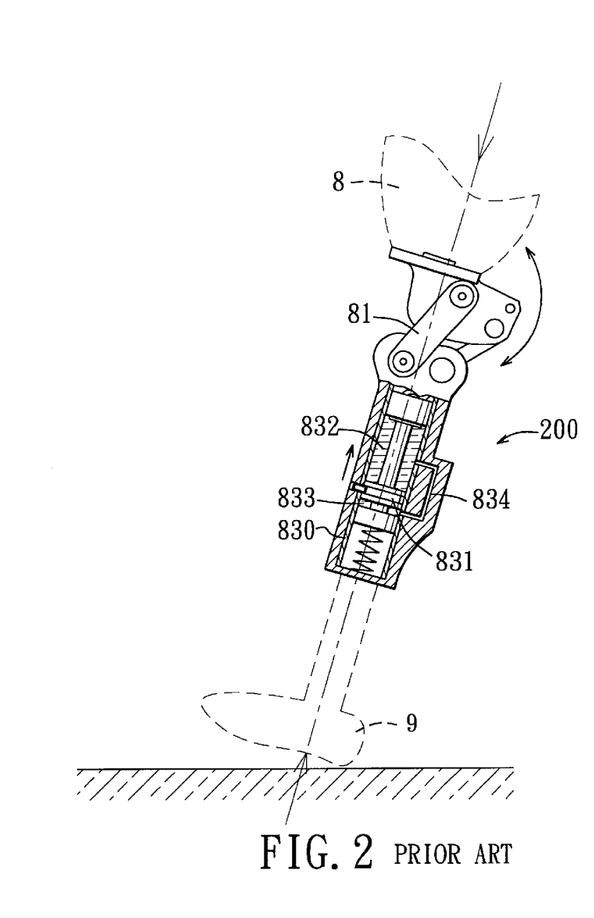
FIG. 2 illustrates how the prosthetic lower leg of the conventional knee joint assembly is about to stand on the ground.

Referring to FIGS. 1 and 2, a conventional artificial knee joint assembly 200 is shown to include a linkage unit 81 connected to a residual thigh 8, a support frame 82 disposed between the linkage unit 81 and a prosthetic lower leg 9, and a damping or hydraulic cylinder unit 83 disposed within the support frame 82. The hydraulic cylinder unit 83 includes a cylinder body 830, a piston 831 disposed movably within the cylinder body 830 so as to divide an interior space in the cylinder body 830 into upper and lower oil chambers 832, 833, and an oil passage 834 formed in the support frame 82 and in fluid communication with the upper and lower oil chambers 832, 833.

When the thigh 8 is raised to separate the artificial knee joint assembly 200 from the ground, as shown in FIG. 1, the lower leg 9 is inclined relative to the thigh 8. As such, the linkage unit 81 moves the piston 831 downwardly within the cylinder body 830, thereby permitting flow of some hydraulic oil from the lower oil chamber 833 into the upper oil chamber 832.

When the artificial knee joint assembly 200 stands on the ground, the linkage unit 81 will move the piston 831 upwardly from a lower limit position shown in FIG. 2 so as to cause some hydraulic oil to flow from the upper oil chamber 832 into the lower oil chamber 833. As such, the lower leg 9 is aligned with the thigh 8 so as to support the same. However, when standing on an inclined surface, the lower leg 9 is inclined relative to the thigh 8 so that the lower leg 9 cannot support the thigh 8, thereby resulting in tumbling of the prosthesis wearer.

SUMMARY OF THE INVENTION

The object of this invention is to provide a safety artificial knee joint assembly that can support effectively a residual thigh on a horizontal or inclined surface.

According to this invention, an artificial knee joint assembly includes a knee seat connected fixedly to a residual thigh, a support frame connected to the knee seat by means of a linkage unit, a prosthetic lower leg connected pivotally to a lower end of the support frame, a hydraulic cylinder unit disposed within the support frame so as to dampen the movement of the support frame relative to the knee seat, and a valve assembly disposed within the support frame. When the lower leg stands on a horizontal or inclined surface, the valve assembly is actuated by the lower leg to stop the operation of the hydraulic cylinder unit, thereby preventing rotation of the lower leg relative to the thigh.

BRIEF DESCRIPTION OF THE DRAWINGS

These and other features and advantages of this invention will become apparent in the following detailed description of the preferred embodiments of this invention, with reference to the accompanying drawings, in which.

DETAILED DESCRIPTION OF THE PREFERRED EMBODIMENTS

Before the present invention is described in greater detail in connection with the preferred embodiments, it should be noted that similar elements and structures are designated by like reference numbers throughout the entire disclosure.

Figure 3:
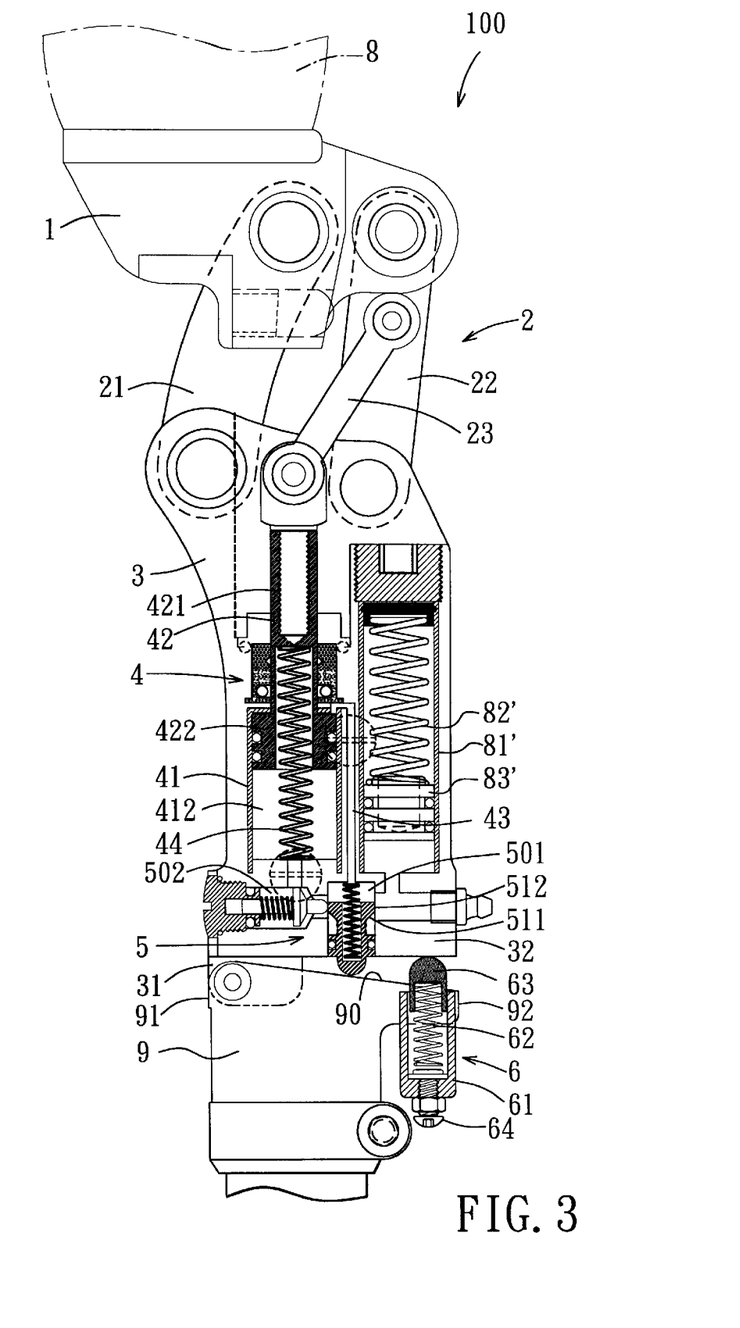
FIG. 3 is a schematic sectional view of the first preferred embodiment of a knee joint assembly according to this invention when an upper rear portion of a prosthetic lower leg is disposed at a first position, where the lower leg does not stand on the ground.
Figure 4:
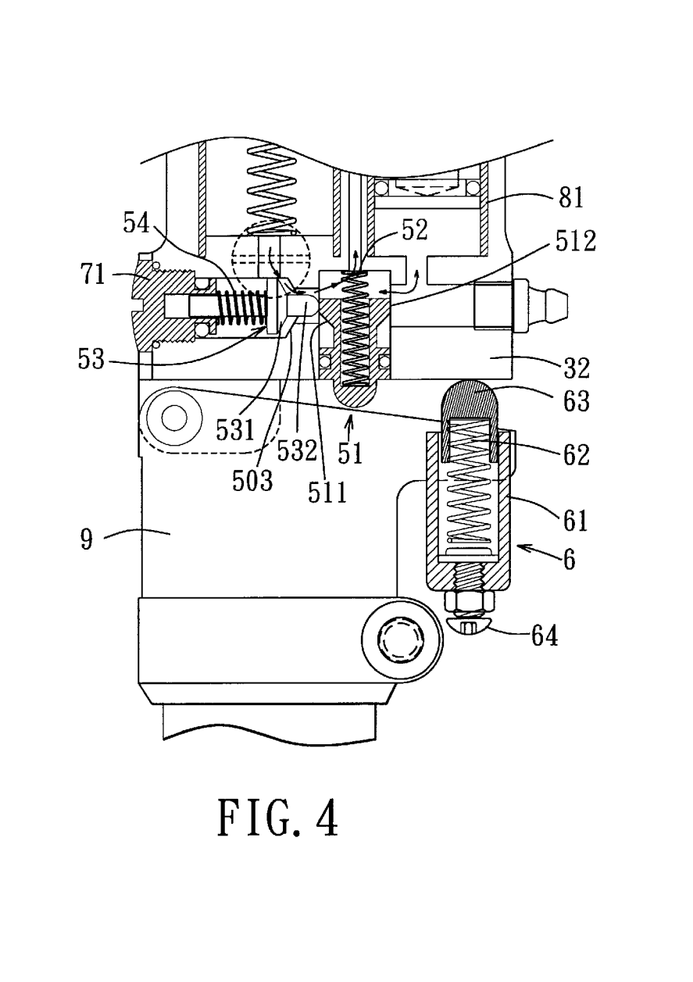
FIG. 4 is an enlarged fragmentary schematic sectional view of the first preferred embodiment, illustrating how hydraulic oil can flow along an oil passage in a support frame when the upper rear portion of the prosthetic lower leg is disposed at the first position.

Referring to FIGS. 3 and 4, the first preferred embodiment of an artificial knee joint assembly 100 according to this invention is shown to include a knee seat 1 connected fixedly to a residual thigh 8 of the prosthesis wearer, a linkage unit 2, a support frame 3, a hydraulic cylinder unit 4, a valve assembly 5, a biasing unit 6, and a prosthetic lower leg 9.

The linkage unit 2 is connected to the knee seat 1, the support frame 3, and the hydraulic cylinder unit 4 in a known manner so as to permit change of a knee angle formed between the knee seat 1 and the support frame 3 and between the thigh 8 and the lower leg 9. The support frame 3 has a lower front portion 31 and a lower rear portion 32. The linkage unit 2 includes first and second links 21, 22 that are connected pivotally to the knee seat 1 and the support frame 3, and a third link 23 that is connected pivotally to the second link 22 and the hydraulic cylinder unit 4. The second link 22 is disposed behind the first link 21.

The lower leg 9 has an upper front portion 91 connected pivotally to the lower front portion 31 of the support frame 3, and an upper rear portion 92 disposed under and adjacent to the lower rear portion 32 of the support frame 3. When the thigh 8 is raised to separate the lower leg 9 from the ground, the upper rear portion 92 of the lower leg 9 is disposed at a first position shown in FIGS. 3 and 4, where the weight of the thigh 8 is not applied to the lower leg 9. When the lower leg 9 stands on the ground, the upper rear portion 92 of the lower leg 9 rotates toward the support frame 3 to a second position shown in FIGS. 5 and 6, where the weight of the thigh is applied to the lower leg 9.

The biasing unit 6 biases the upper rear portion 91 of the lower leg 9 to turn away from the lower rear portion 32 of the support frame 3, and includes a vertical hollow cylinder 61, a coiled compression spring 62, a cap 63, and a vertical adjustment bolt 64. The hollow cylinder 61 is disposed fixedly within the upper rear portion 92 of the lower leg 9, and has an open upper end and a lower end wall. The coiled compression spring 62 is disposed within the hollow cylinder 61. The cap 63 is retained on an upper end of the coiled compression spring 62, extends from the upper end of the hollow cylinder 61, and is biased by the coiled compression spring 62 to press against the lower rear portion 32 of the support frame 3 so that the upper rear portion 92 of the lower leg 9 is disposed at the first position when the lower leg 9 does not stand on the ground. The vertical adjustment bolt 64 is connected threadedly to the lower end wall of the hollow cylinder 61 so as to permit adjustment of the biasing force of the coiled compression spring 62.

The hydraulic cylinder unit 4 is disposed within the support frame 3 so as to dampen the movement of the support frame 3 relative to the knee seat 1, and includes a cylinder body 41, a piston member 42, an oil passage 43, and a resilience member 44 that is shaped as a coiled compression spring. The piston member 42 is disposed movably within the cylinder body 41, and divides an interior space in the cylinder body 41 into upper and lower oil chambers 411, 412. The oil passage 43 is formed in the support frame 3, and is in fluid communication with the upper and lower oil chambers 411, 412 in the cylinder body 41 so as to permit hydraulic oil flow between the upper and lower oil chambers 411, 412 when the upper rear portion 92 of the lower leg 9 is disposed at the first position shown in FIGS. 3 and 4. The piston member 42 includes a piston rod 421 connected pivotally to the third link 23 of the linkage unit 2, and a piston 422. Because the piston rod 421 occupies a relatively large volume of the upper oil chamber 411, when the piston member 42 moves downward within the cylinder body 41 from the position shown in FIG. 3 to that shown in FIG. 5, the volume of the hydraulic oil in the lower oil chamber 412 which is reduced is larger than that in the upper oil chamber 411 which is increased, whereby some hydraulic oil flows from the upper oil chamber 411 into an oil storage cylinder 81' to compress a spring 82' in the oil storage cylinder 81'. Subsequently, when the piston member 42 moves upward within the cylinder body 41 from the position shown in FIG. 5 to that shown in FIG. 3, the spring 82' stretches so that a piston 83' urges the hydraulic oil within the storage oil cylinder 81' to flow back into the upper oil chamber 411.

The valve assembly 5 is disposed within the support frame 3, and includes a hollow first valve 51, a first spring 52, a second valve 53, and a second spring 54. A vertical slot 501 is formed in a bottom surface of the support frame 3, and is in fluid communication with the upper chamber 411 in the cylinder body 41. The first valve 51 is disposed sealingly, vertically, and movably within the vertical slot 501 in the support frame 3, and has a lower end projecting downwardly from the bottom surface of the support frame 3 to extend into a space between the support frame 3 and the lower leg 9, a frustoconical neck portion 511 having a diameter that reduces downwardly, and a cylindrical head portion 512 having a lower end that is formed integrally with an upper end of the neck portion 511. The first spring 52 extends into the first valve 51, and biases the first valve 51 to move downwardly so that the lower end of the first valve 51 contacts an inclined top surface 90 of the lower leg 9 when the upper rear portion of the lower leg 9 is disposed at the first position shown in FIGS. 3 and 4. A horizontal slot 502 is formed in the support frame 3, and is in fluid communication with the vertical slot 501 and the lower oil chamber 412 in the cylinder body 41. The second valve 53 is constructed as a poppet valve, is disposed sealingly, horizontally, and movably within the horizontal slot 502 in the support frame 3, and has a frustoconical valve body 531 confined within a frustoconical portion 503 of the horizontal slot 502 so as to prevent movement of the valve body 531 into the vertical slot 501, and a rounded head portion 532 movable to extend into the vertical slot 501. The second spring 54 biases the rounded head portion 532 of the second valve 53 to press against the head portion 512 of the first valve 51 when the upper rear portion 92 of the lower leg 9 is disposed at the first position shown in FIGS. 3 and 4. When the upper rear portion 92 of the lower leg 9 rotates from the first position shown in FIGS. 3 and 4 to the second position shown in FIGS. 5 and 6, the lower end of the first valve 51 is pushed upwardly by the lower leg 9. As such, the rounded head portion 532 of the second valve 53 moves downwardly from the head portion 512 of the first valve 51 onto the frustoconical neck portion 511 of the first valve 51 so as to prevent downward movement of the first valve 51 against biasing action of the first spring 52, thereby stopping the hydraulic oil flow between the upper and lower oil chambers 411, 412 in the cylinder body 41, which in turn prevents movement of the support frame 3 relative to the knee seat 1. Accordingly, even if the lower leg 9 stands on an inclined surface, it will activate the valve assembly 5 so as to stop the hydraulic oil flow between the upper and lower oil chambers 411, 412 in the cylinder body 41, thereby supporting effectively the thigh 8 on the lower leg 9 and enhancing the safety of the artificial knee joint assembly. Therefore, the intended object of this invention can be achieved.

A first upper horizontal adjustment bolt 71 is mounted threadedly to the support frame 3, and is connected to the second spring 54 so as to permit adjustment of the biasing force of the second spring 54.

Figure 5:
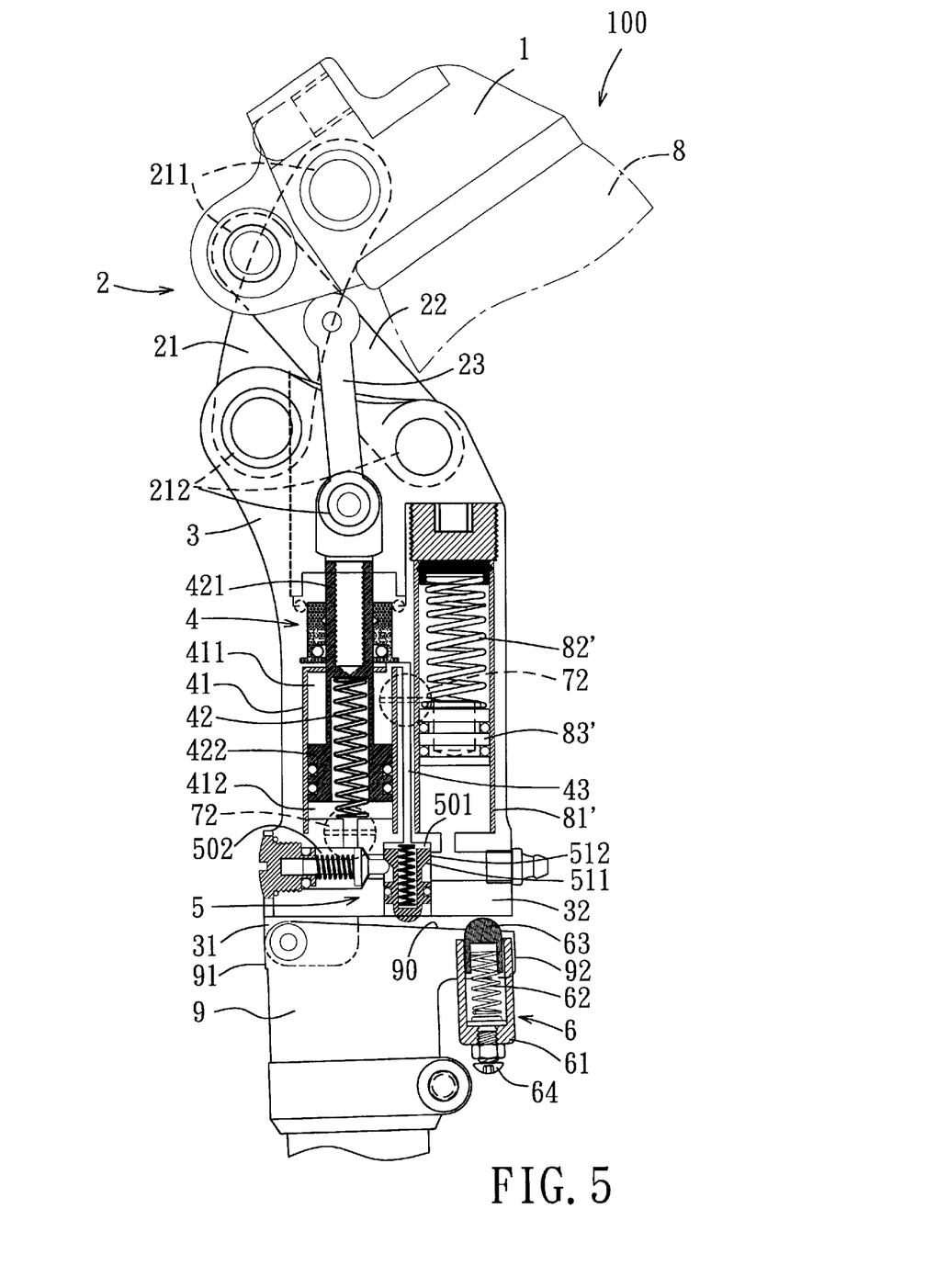
FIG. 5 is a schematic sectional view of the first preferred embodiment when the upper rear portion of the lower leg is disposed at a second position, where the lower leg stands on the ground.
Figure 6:
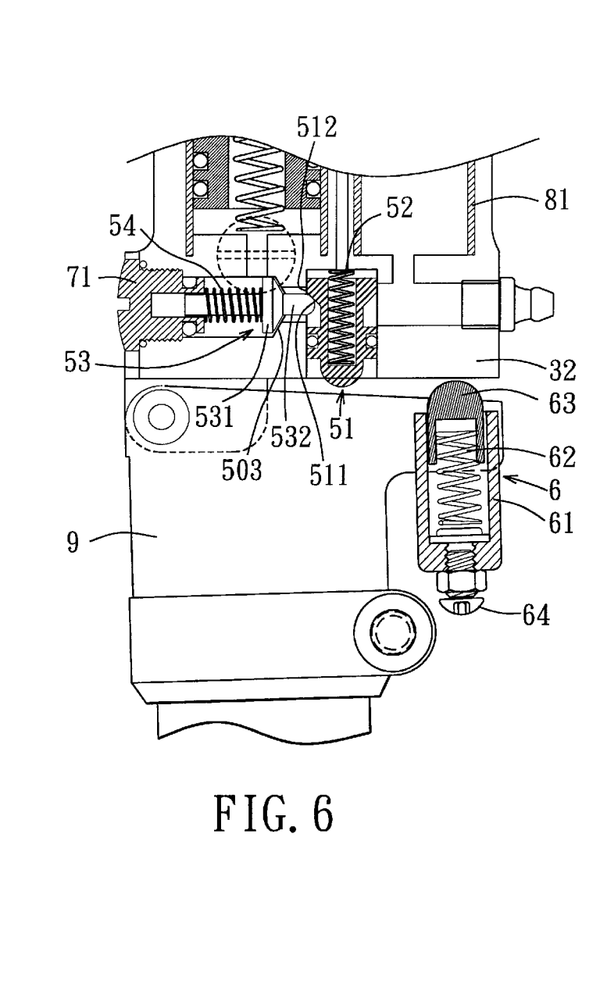
FIG. 6 is an enlarged fragmentary schematic sectional view of the first preferred embodiment, illustrating how hydraulic oil is prevented from flowing along the oil passage when the upper rear portion of the lower leg is disposed at the second position.
Figure 7:
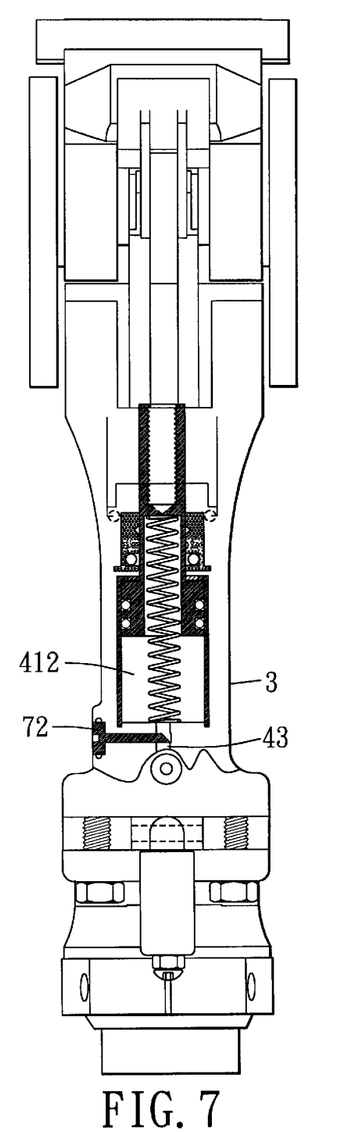
FIG. 7 illustrates how a second upper horizontal adjustment bolt is provided on the support frame of the first preferred embodiment so as to permit adjustment of flow rate of the hydraulic oil along the oil passage.
Figure 8:
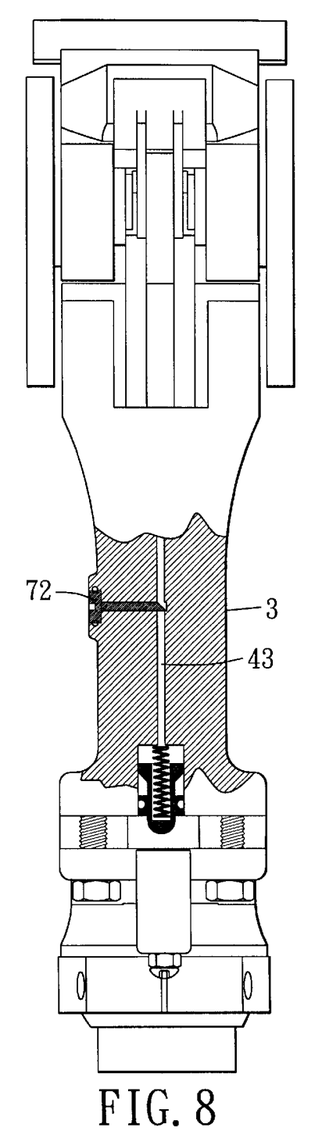
FIG. 8 illustrates how another second upper horizontal adjustment bolt is provided on the support frame of the first preferred embodiment so as to permit adjustment of the flow rate of the hydraulic oil along the oil passage.

Referring to FIGS. 5, 7 and 8, two second upper horizontal adjustment bolts 72 are mounted threadedly to the support frame 3, and are arranged one above another. Each of the second upper horizontal adjustment bolts 72 has a portion that extends into the oil passage 43 in the support frame 3 so that the volume of the portions of the second upper horizontal adjustment bolts 72 in the oil passage 43 can be adjusted, thereby varying the flow rate of the hydraulic oil between the upper and lower oil chambers 411, 412 in the cylinder body 41.

Figure 9:
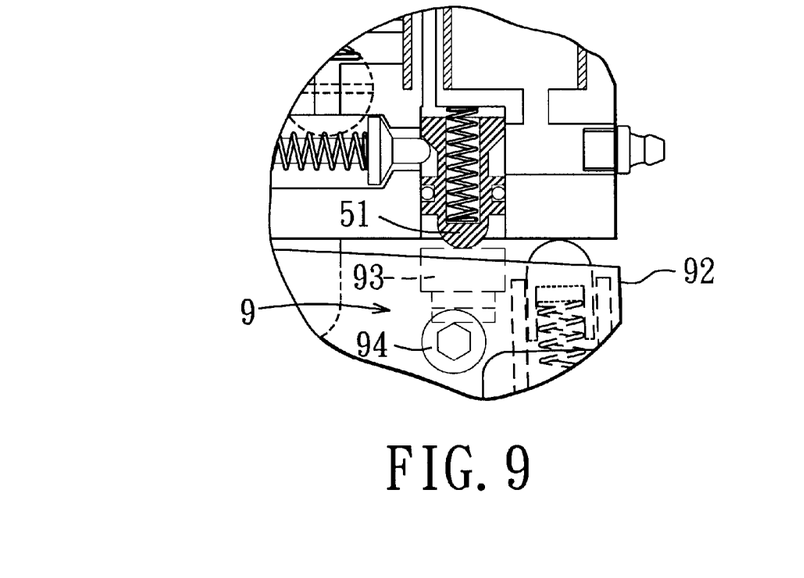
FIGS. 9 and 10 are schematic fragmentary sectional views of the second preferred embodiment of an artificial knee joint assembly according to this invention.
Figure 10:
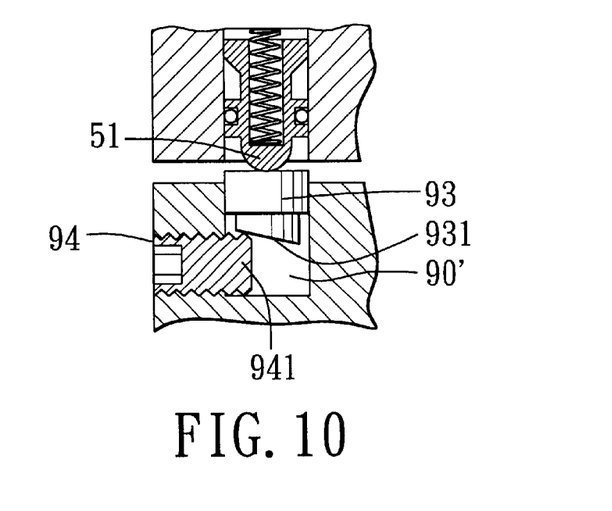

FIGS. 9 and 10 show the second preferred embodiment of an artificial knee joint assembly of this invention. Unlike the previous embodiment, the lower leg 9 further has a vertical hole 90' formed in the top surface thereof, a pressing element 93, and a lower horizontal adjustment bolt 94. The pressing element 93 is disposed vertically and movably within the vertical hole 90', and has an inclined bottom surface 931, and a top surface that projects from the vertical hole 90' and that is disposed under the first valve 51. The lower horizontal adjustment bolt 94 has an inner end 941 that abuts against the bottom surface 931 of the pressing element 93 so that actuation of the lower horizontal adjustment bolt 94 can result in vertical movement of the pressing element 93 within the vertical hole 90', thereby permitting adjustment of a distance between the first valve 51 and the pressing element 93 when the upper rear portion 92 of the lower leg 9 is disposed at the first position.

With this invention thus explained, it is apparent that numerous modifications and variations can be made without departing the scope and spirit of this invention. It is therefore intended that this invention be limited only as indicated by the appended claims.

I claim:

1. An artificial knee joint assembly adapted to be mounted on a residual thigh of a prosthesis wearer, said artificial knee joint assembly comprising:
   a knee seat adapted to be connected fixedly to the residual thigh;
   a linkage unit connected to said knee seat;
   a support frame connected to said linkage unit so as to permit change of a knee angle formed between said knee seat and said support frame, said support frame having a lower front portion and a lower rear portion;
   a prosthetic lower leg having an upper front portion connected pivotally to said lower front portion of said support frame, and an upper rear portion disposed under and adjacent to said lower rear portion of said support frame, said upper rear portion of said lower leg being disposed at a first position when said lower leg does not stand on the ground, and being rotatable toward said support frame to a second position when said lower leg stands on the ground;
   a biasing unit for biasing said upper rear portion of said lower leg to turn away from said lower rear portion of said support frame;
   a hydraulic cylinder unit disposed within said support frame and including
      a cylinder body defining an interior space;
      a piston member disposed movably within said cylinder body and dividing said interior space in said cylinder body into an upper oil chamber and a lower oil chamber,
      an oil passage formed in said support frame and in fluid communication with said upper and lower oil chambers in said cylinder body so as to permit hydraulic oil flow between said upper and lower oil chambers when said upper rear portion of said lower leg is disposed at said first position, and
      a resilience member for biasing said piston member to move upwardly within said cylinder body; and
   a valve assembly disposed within said support frame and having a portion that extends into a space between said support frame and said lower leg, said valve assembly being actuated by said support frame so as to stop the hydraulic oil flow between said upper and lower oil chambers in said cylinder body when said upper rear portion of said lower leg is disposed at said second position, thereby fixing position of said knee seat relative to said support frame.

2. The artificial knee joint assembly as claimed in claim 1, wherein said support frame has a bottom surface, said valve assembly includes:
   a vertical slot formed in said bottom surface of said support frame and in fluid communication with said upper chamber in said cylinder body;
   a first valve disposed sealingly, vertically, and movably within said vertical slot in said support frame and having a lower end projecting downwardly from said bottom surface of said support frame, a frustoconical neck portion having a diameter that reduces downwardly, and a cylindrical head portion having a lower end that is formed integrally with an upper end of said neck portion;
   a first spring for biasing said first valve to move downwardly so that said lower end of said first valve contacts said lower leg when said upper rear portion of said lower leg is disposed at said first position;
   a horizontal slot formed in said support frame and in fluid communication with said vertical slot and said lower oil chamber in said cylinder body;
   a second valve disposed sealingly, horizontally, and movably within said horizontal slot in said support frame and having a rounded head portion movable to extend into said vertical slot in said support frame;
   a second spring for biasing said rounded head portion of said second valve to press against said head portion of said first valve when said upper rear portion of said lower leg is disposed at said first position, said rounded head portion of said second valve being urged to press against said frustoconical neck portion of said first valve when said upper rear portion of said lower leg is disposed at said second position, where said lower end of said first valve is pushed upwardly by said lower leg, so as to prevent downward movement of said first valve against biasing action of said first spring, thereby stopping the hydraulic oil flow between said upper and lower oil chambers in said cylinder body.

3. The artificial knee joint assembly as claimed in claim 2, further comprising a first upper horizontal adjustment bolt that is mounted threadedly to said support frame and that is connected to said second spring so as to permit adjustment of biasing force of said second spring.

4. The artificial knee joint assembly as claimed in claim 2, further comprising a second upper horizontal adjustment bolt that is mounted threadedly to said support frame and that has a portion, which extends into said oil passage in said support frame so that volume of said portion of said second upper horizontal adjustment bolt in said oil passage can be adjusted, thereby varying flow rate of the hydraulic oil between said upper and lower oil chambers in said cylinder body.

5. The artificial knee joint assembly as claimed in claim 2, wherein said lower leg further has:
   a top surface with a vertical hole;
   a pressing element disposed vertically and movably within said vertical hole and having an inclined bottom surface and a top surface that projects from said vertical hole and that is disposed under said first valve; and
   a lower horizontal adjustment bolt mounted threadedly to said lower leg and having an inner end that abuts against said bottom surface of said pressing element so that actuation of said lower horizontal adjustment bolt can result in vertical movement of said pressing element within said vertical hole, thereby permitting adjustment of a distance between said first valve and said pressing element when said upper rear portion of said lower leg is disposed at said first position.

6. The artificial knee joint assembly as claimed in claim 1, wherein said biasing unit includes:
   a vertical hollow cylinder disposed fixedly within said upper rear portion of said lower leg and having an open upper end and a lower end wall;
   a coiled compression spring disposed within said hollow cylinder; and a cap retained on an upper end of said coiled compression spring and extending from said upper end of said hollow cylinder, said cap being biased by said compression spring to press against said lower rear portion of said support frame so that said upper rear portion of said lower leg is disposed at said first position when said lower leg does not stand on the ground.

7. The artificial knee joint assembly as claimed in claim 6, further comprising a vertical adjustment bolt that is connected threadedly to said lower end wall of said hollow cylinder of said biasing unit so as to permit adjustment of biasing force of said coiled compression spring.

* * * * *